United States Patent [19]

Atlas

[11] Patent Number: 4,630,614
[45] Date of Patent: Dec. 23, 1986

[54] APNEA MONITORING APPARATUS

[76] Inventor: Dan Atlas, Mashabim 20, Hod Hasharon, Israel

[21] Appl. No.: 708,416

[22] Filed: Mar. 5, 1985

[30] Foreign Application Priority Data

Apr. 8, 1984 [IL] Israel ................................. 71468

[51] Int. Cl.⁴ ............................................. A61B 5/08
[52] U.S. Cl. .................................... 128/721; 128/726
[58] Field of Search ....................... 128/670, 721–724, 128/734

[56] References Cited

U.S. PATENT DOCUMENTS

| | | | |
|---|---|---|---|
| 3,572,317 | 10/1968 | Wade | 128/696 |
| 3,802,419 | 4/1974 | Yates | 128/723 |
| 3,875,929 | 4/1975 | Grant | 128/721 |
| 3,911,899 | 10/1975 | Hattes | 128/721 |
| 4,036,217 | 7/1977 | Ito et al. | 128/723 |
| 4,269,195 | 5/1981 | Itoh | 128/723 |
| 4,281,651 | 8/1981 | Cox | 128/204.23 |
| 4,289,142 | 9/1981 | Kearns | 128/723 |
| 4,421,113 | 12/1983 | Gedeon et al. | 128/204.23 |
| 4,449,537 | 5/1984 | Pross et al. | 128/723 |

OTHER PUBLICATIONS

"Non Invasive Respiratory Function Monitoring System".

Primary Examiner—Kyle L. Howell
Assistant Examiner—David Shay
Attorney, Agent, or Firm—Benjamin J. Barish

[57] ABSTRACT

A method and apparatus for monitoring a subject to detect the occurrence of apnea, wherein the respiration rate and amplitude of the subject is detected by a plurality of electrodes for a predetermined initial time interval of a plurality of breath to produce a measure of the average respiration volume of the subject, the latter measurement is stored, and is compared with the detected respiration rate and amplitude of the subject during subsequent time intervals. A signal is generated whenever a detected average volume falls below the reference average volume by a predetermined percentage.

8 Claims, 4 Drawing Figures

FIG. 3
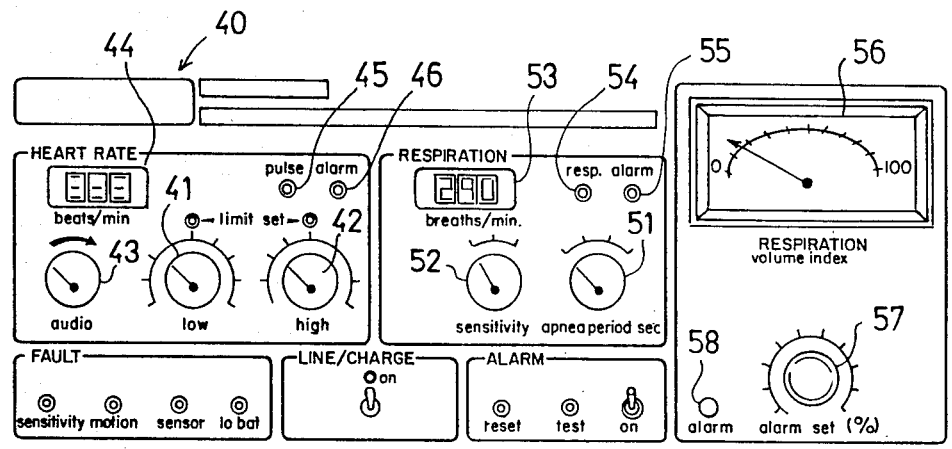
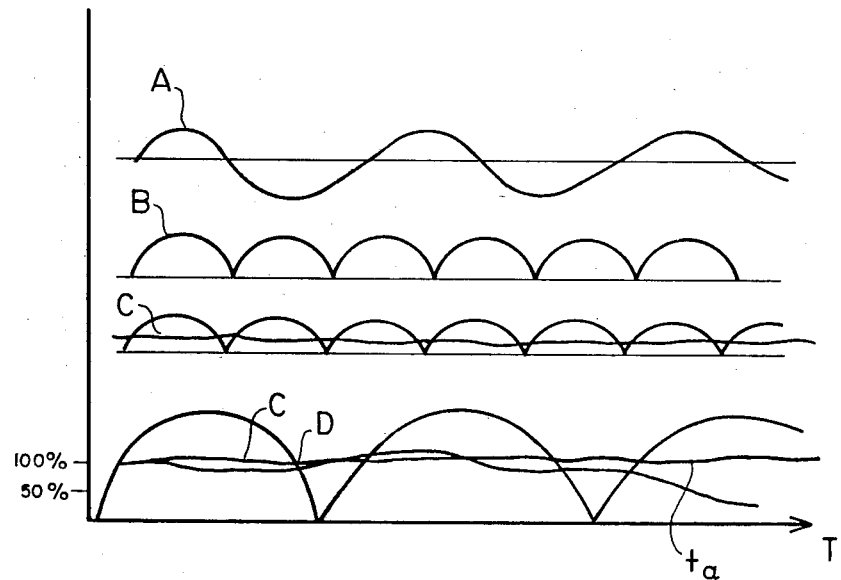
FIG. 4

APNEA MONITORING APPARATUS

BACKGROUND OF THE INVENTION

The present invention relates to apparatus for monitoring the respiratory condition of a subject, and particularly for detecting the occurrence of apnea.

Reliable detection of apnea, namely a transient suspension of respiration, is a very serious problem which has not yet been successfully solved. Many techniques and devices have been developed for detecting apnea, but the known techniques are still not entirely satisfactory. Thus, some of the known systems monitor for apnea by detecting gross body movements, such as by the use of a mattress. However, in the event of an upper airway obstruction, such as by vomit or any other condition causing suffocation, the patient usually enters into twitching or other frantic movements during which no air passes through the lungs, but the physical activity prevents the actuation of the apnea alarm so that the apnea condition may go unnoticed until actual unconsciousness or death occurs. Other techniques for monitoring respiration in order to detect apnea include a thermistor or other transducer near the subject's nostrils to detect breathing, elastic tubes around the subject's chest to detect its expansion and contraction caused by breathing, or a microphone to detect the sounds produced by the subject when breathing. Such techniques, however, are not completely reliable particularly where the apnea is caused by an upper airway obstruction. About the only present technique for detecting apnea caused by an upper airway obstruction is by the use of a mask which monitors the $CO_2$ exhaled by the patient, but this technique is very obstrusive; and moreover the mask tends to become clogged by mucous thereby losing its efficacy.

SUMMARY OF THE INVENTION

An object of the present invention is to provide apparatus for monitoring a subject to detect the occurrence of apnea, which apparatus is non-obtrusive, and can detect all conditions of apnea even those caused by an upper airway obstruction.

According to the present invention, there is provided apparatus for monitoring a subject to detect the occurrence of apnea, comprising a plurality of electrodes to be applied to spaced points on the subject for detecting the respiration rate and respiration amplitude of the subject by the change in electrical impedance between the spaced points; computing means including an average circuit averaging the detected respiration rate and respiration amplitude over a predetermined time interval covering a plurality of breaths of the subject and computing therefrom the average respiration volume of the subject; storage means for storing, as a reference average volume, the average respiration volume of the subject during an initial time interval, and also for storing, as current average volumes, the average respiration volume of the subject during subsequent time intervals; comparing means for comparing each of the current average respiration volumes with the reference average respiration volume; and signalling means actuated to indicate the occurrence of apnea whenever a current average respiration volume falls below the reference average respiration volume by a predetermined percentage.

According to another important feature in the preferred embodiment of the invention described below, the apparatus further includes means for detecting gross body movements of the subject and for ignoring, from the computations of the reference average volume and the current average volumes, the respiration rate and amplitude of the subject detected when the gross body movement exceed a predetermined magnitude.

As will be more apparent from the description below, the apparatus can detect generally all apnea conditions, including that caused by an upper airway obstruction. In addition, the apparatus is nonobstructive, and further, it can be implemented by apparatus which, for the most part, includes components presently available in existing apparatus for monitoring respiration and/or heart activity. A further advantage is that the method and apparatus are self-adaptive for each subject to be monitored.

Further features and advantages of the invention will be apparent from the description below

BRIEF DESCRIPTION OF THE DRAWINGS

The invention is herein described, by way of example only, with reference to the accompanying drawings, wherein:

FIG. 3 illustrates the control panel in the apnea monitor of FIG. 2; and

FIG. 4 illustrates a set of waveforms helpful in understanding the apnea monitoring method and apparatus of the present invention.

DESCRIPTION OF A PREFERRED EMBODIMENT

Figure 1:
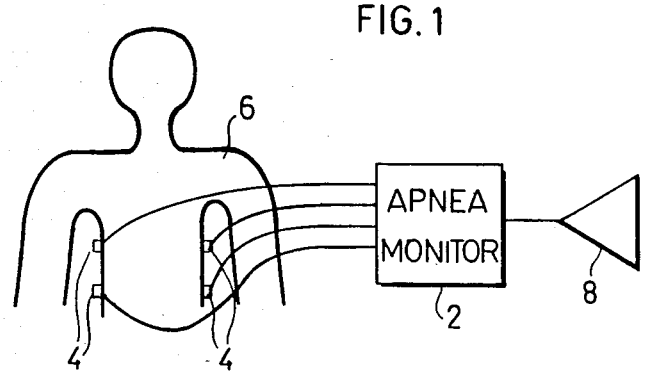
FIG. 1 schematically illustrates the use of an apnea monitor for detecting apnea in a subject.

FIG. 1 schematically illustrates an apnea monitor, therein designated 2, including a plurality of electrodes 4 applied to spaced points on the subject 6 for monitoring the subject with respect to respiration activity such that should there occur a suspension of respiration indicating apnea, the monitor 2 actuates an alarm 8. As indicated earlier, a large number of apnea monitors of this type have been devised. The known monitors include two, three or four electrodes which measure respiration by changes in the impedance between the spaced points at whch the electrodes 4 are applied. In some known systems, the electrodes 4 also detect heart rate activity, enabling monitor 2 also to detect the heart rate.

Figure 2:
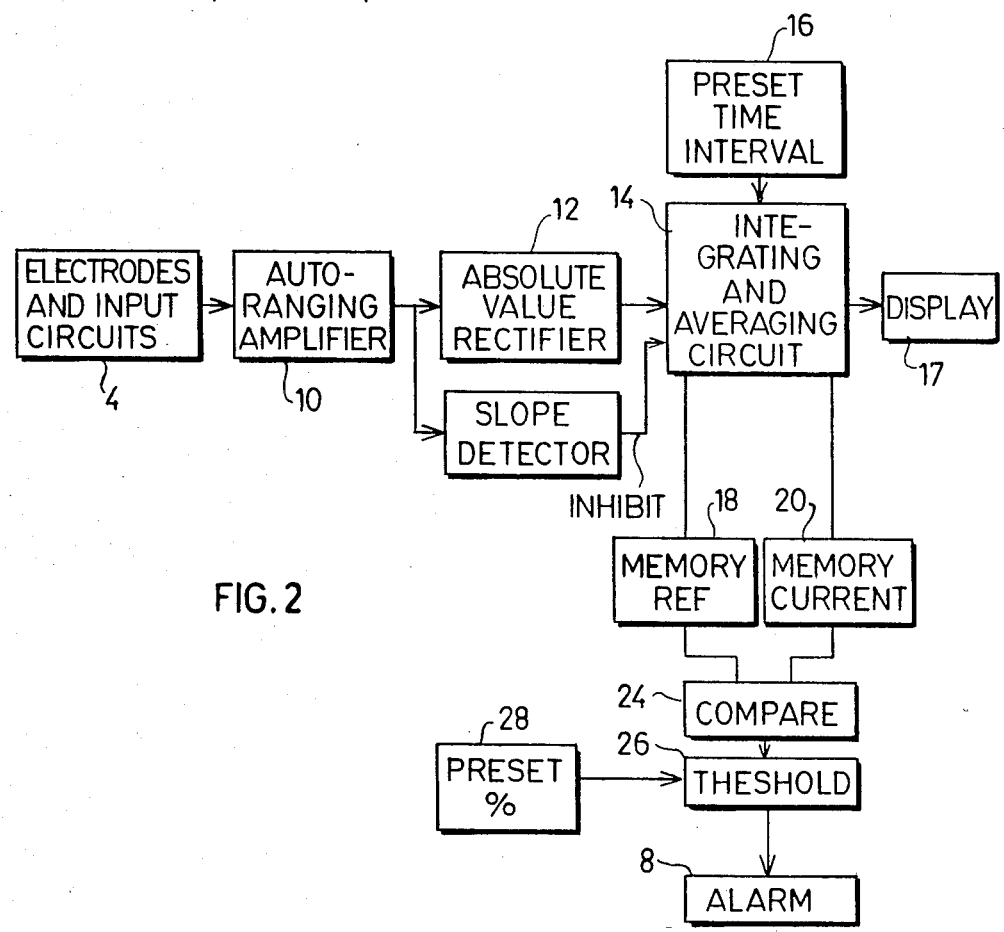
FIG. 2 is a block diagram illustrating one form of apnea monitor constructed in accordance with the present invention for detecting upper airway obstructions.

The portion of monitor 2 for detecting apnea in accordance with the present invention is more particularly illustrated in the block diagram of FIG. 2. The control panel of the novel apnea monitor constructed in accordance with the present invention is illustrated in FIG. 3, wherein it will be seen that it detects both respiration activity and heart rate activity, but its primary function is to monitor for apnea as will be described more particularly below.

Thus, as shown in FIG. 2, the monitor 2 includes an auto-ranging amplifier 10 for receiving the output of the electrodes 4 applied to the subject. In the type of monitor illustrated in the drawings, the electrodes 4 produce an electrical analog signal having a waveform corresponding to the respiration rate and amplitude of the subject. The latter signal is illustrated by waveform A in FIG. 4. This electrical signal, after amplification in amplifier 10, is inputted into an absolute value rectifier 12 which converts the negative-going portions of the signal to positive-going signals, as illustrated by curve B in FIG. 4.

The output of the absolute value rectifier 12 is then fed to an integrating and averaging circuit 14 which integrates the waveforms over a predetermined time period, as preset by a manipulatable device 16 and averages the integrated waveforms over the predetermined time interval. The output of circuit 14 is an averaging value, as shown by line C in FIG. 4, representing the average respiration volume of the subject's respiration during the predetermined time interval. The average respirations per minute and/or volume for the respective time period may be displayed in display 17.

When initially using the apparatus, the average volume from circuit 14 is stored in memory 18 and constitutes a reference, or baseline, average volume representing the average respiration volume during this initial time interval. Subsequently, the average volume from circuit 14 is stored in a second memory 20, such that the latter memory stores the average volume representing the average respiration volume during each subsequent time interval. The value in memory 20 is thus designated the current average volume and is continuously updated for each subsequent time interval; the reference average volume, however, which is computed and stored in memory 18 during the initial time interval, is not changed but remains constant.

At the end of each of the predetermined time intervals subsequent to the initial time interval, the respective current average volume stored in memory 20 is compared with the reference average volume stored in memory 18 by a compare circuit 24 to determine the relationship between the two, namely the percentage drop or rise of the current average volume in the respective time with respect to the reference average volume determined at the initial time interval. A threshold circuit 26, manually presettable by a presettable member 28, fixes a particular percentage for actuating the alarm 8. That is, if the current average volume stored in memory 20 falls below the reference average volume stored in memory 18 by the preset percentage, alarm 8 is actuated.

The illustrated system further includes means for detecting gross body movement of the subject and for ignoring, from the computations of both the reference average volume and the current average volumes, the respiration rate and amplitude of the subject whenever such gross body movements exceed a predetermined magnitude. For this purpose, the illustrated circuit includes a slope detector 30 receiving the analog waveform from amplifier 10. Slope detector 30 continuously measures the slope of the waveform, and whenever it determines that the slope has exceeded a predetermined magnitude indicating excessive body movement, it controls the integrating and averaging circuit 14 to cause the circuit to ignore the analog waveforms then being generated from the integrating and averaging operations. These waveforms are ignored both during the initial time interval when the reference average volume is determined and stored in memory 18, and also during each subsequent time interval when the subsequent current average volumes are measured and stored in memory 20.

It will thus be seen that the system illustrated in FIG. 2 first determines and stores in memory 18 the average respiration volume of the subject during an initial time interval and uses same as a reference or baseline for comparing the subject's average respiration volume stored in memory 20 in each subsequent time interval; and whenever an average volume falls below the reference average volume by a predetermined percentage, alarm 8 is actuated. The predetermined percentage may be manually preset by member 28; for example, member 28 may be preset from 30–70% to actuate alarm 8 whenever a current average volume falls to 30–70% of the reference average volume, a preferred percentage being about 50%. The time interval, for determining both the initial reference average volume and the subsequent current average volumes, may be preset by presettable member 16; preferably, this time interval is from 7.5–20 seconds, a preferred time interval being about 10 seconds.

FIG. 3 illustrates one specific control panel 40 which may be used for implementing the apparatus of FIG. 2. As indicated earlier, the monitor illustrated by control panel 40 shown in FIG. 3 is intended not only for monitoring apnea, but also for monitoring heart rate activity. The heart rate activity is detected by the same electrodes 4 used for detecting respiration activity as known in monitors of this type. The monitor circuitry for processing the heart rate activity in order to produce the displays and indications illustrated in the control panel of FIG. 3 is also very well known and is therefore not described herein.

As shown in FIG. 3, control panel 40 includes a "low" and "high" knob 41, 42, respectively, for presetting the heart rate limit, and an "audio" knob 43 which presets the audio intensity of the "beep" sounded by the apparatus for each heartbeat. The control panel further includes a digital display 44 for displaying the heart rate, a "pulse" light indicator 45 which is energized for each heart pulse, and an "alarm" indicator 46 which is energized should the heart rate be less than, or greater than, the limits preset by knobs 41 and 42. As indicated earlier, known circuitry may be used for performing the above operations with respect to heart rate activity.

The portion of the control panel illustrated in FIG. 3 used for monitoring respiratory activity to detect the occurrence of apnea includes a manipulatable knob 51 for presetting the apnea period during which at least one breath must be detected before the normal alarm is energized. This is to be distinguished from the predetermined time interval during which the initial reference average volume, and the subsequent current average volumes, are to be determined, this latter interval being prefixed, e.g. from 7.5 to 20 seconds, preferably at 10 seconds. Control panel 40 further includes a sensitivity knob 52 for presetting the sensitivity of the apparatus, according to any one of three general types of subjects (e.g. baby, child, adult) with which the apparatus is to be used. Knob 52 controls the range and/or gain of amplifier 10 in FIG. 2.

Control panel 40 further includes a digital display 53 for displaying the respiration rate in breaths/minute, which may correspond to display 17 in FIG. 2; a light indicator 54 which is energized during each breath; a further light indicator 55 which is energized whenever an "alarm" condition is detected; and a display 56 for displaying, in percentages, the relation that each current average volume stored in memory 20 bears to the initial reference average volume stored in memory 18. Display 56 is preferably of the analog type, graduated from zero to 100%, to show this relationship in percentage points.

Control panel 40 further includes a rotatable knob 57, corresponding to presettable member 26 in FIG. 2, enabling the user to preset the percentage between the current average volume and the reference average volume below which the alarm (8, FIG. 1) will be actuated to signal an apnea condition. A further indicator lamp 58 on the control panel is energized whenever the alarm is actuated.

Control panel 40 includes the following additional switches and indicators: mains switch 60 for connecting apparatus to the electrical supply mains; switch 61 for enabling the alarm to be actuated when an apnea condition is detected as described above; push-button switch 52 for testing the apparatus; reset switch 63 for resetting the apparatus; light indicator 64 which is energized if the sensitivity knob 52 is not properly set for the subject being mounted; light indicator 65 which is energized if excessive body movement of the subject is detected; light indicator 66 which is energized if an electrode falls off the subject being monitored; and light indicator 67 which is energized if the battery supply is too low. The latter controls and indicator lamps are commonly included in heart and respiration monitoring apparatus, and therefore the corresponding circuits involved are not disclosed herein.

The manner of using the illustrated apparatus will be apparent from the above description. Thus, electrodes 4 (FIG. 1) are applied to the subject in the manner commonly used for monitoring heart and respiration activity. Knobs 41, 42 and 43 of control panel 40 (FIG. 3) may be preset in the conventional manner for monitoring heart activity.

With respect to respiration activity, knob 52 is preset to select the sensitivity appropriate for subject being monitored, e.g. (1) baby; (2) child; or (3) adult. Knob 51 is then preset to select the time interval (e.g. from 7.5 to 20 seconds) during which at least one breath must be detected before energizing the alarm. The apparatus is prefixed with the predetermined time interval (e.g. 10 seconds) during which the averaging operations are to be performed in both modes of operation of the apparatus, namely (1) the initial mode, to produce a reference average volume representing the average respiration volume of the subject during the initial time interval; and (2) the current mode, to produce a current average volume representing the average respiration volume of the subject during each subsequent time interval.

Knob 57 is then set by the user to select the percentage by which a fall of a current average volume, with respect to the initial reference average volume, will trigger the alarm (8, FIG. 1). Knob 57 may be graduated from 0% to 100%. The actual percentage computed during the operation of the apparatus is displayed in display 56.

After the apparatus has been preset as described above, the electrodes 4 detect the respiration activity of the subject being monitored and produce an electrical analog signal, illustrated at A in FIG. 4, corresponding to the respiration rate and volume of the subject being monitored. This electrical analog signal, after being amplified in amplifier 10 (FIG. 2) is fed to the absolute value rectifier 12 where its negative-going portions are converted to positive-going signals, as shown by waveforms B in FIG. 4. The rectified waveforms are fed to integrating and averaging circuit 14, which produces an average value, represented by level C in FIG. 4, corresponding to the average respiration volume of the subject during the prefixed time interval, e.g. 10 secs. This value is stored in memory 18 of FIG. 2.

The monitoring of the patient may then be effected for subsequent time intervals, each corresponding to that prefixed. Thus, if the apparatus had been prefixed for 10 second intervals, then each 10 seconds subsequent to the initial 10 seconds when the reference volume was determined, the electrical waveforms detected by electrodes 4, after having been amplified and rectified, are integrated and averaged by circuit 14 to produce a current average volume representing the average respiration volume of the subject during the respective time interval. This current average volume is indicated by level D in FIG. 4; that value is stored in the current memory 20 and is continuously compared in comparison circuit 24 with the reference average volume stored in memory 18. Whenever the current average volume D falls below the reference average volume C by the percentage preset by knob 57 (e.g. 50%), alarm 8 is triggered to signal this condition. The latter condition is indicated at time $t_a$ in FIG. 4.

While the subject's respiration activity is being monitored as described above, during both the initial time interval when the reference average volume is computed, and each subsequent time interval when the respective current average volume is computed, the respiration activity of the subject occurring during gross body movements are ignored. Slope detector 30 (FIG. 2) detects gross bodily movement, and applies an inhibit signal to the integrating and averaging circuit 15 causing the latter circuit to disregard these activities occurring at these times.

While the invention has been described with respect to one preferred embodiment, it will be appreciated that many variations may be made, For example, the apparatus, particularly that portion illustrated in FIG. 2, could be implemented by a microprocessor programmed to perform the functions set forth. In addition, the respiration rate and amplitude of the subject could be detected by other forms of detectors than electrodes measuring changes in inpedance; for example, there could be used electric tubes around the subject's chest; nostril thermistors, or other transducers, which convert air flow into analog signals. Many other variations, modifications and applications of the invention will be apparent.

What is claimed is:

1. Apparatus for monitoring a subject to detect the occurrence of apnea, comprising:
    a plurality of electrodes to be applied to spaced points on the subject for detecting the respiration rate and respiration amplitude of the subject by the change in electrical impedance between said spaced points;
    computing means including an averaging circuit averaging the detected respiration rate and respiration amplitude over a predetermined time interval covering a plurality of breaths of the subject and computing therefrom the average respiration volume of the subject;
    storage means for storing, as a reference average volume, the average respiration volume of the subject during an initial time interval, and also for storing, as current average volumes, the average respiration volume of the subject during subsequent time intervals;
    comparing means for comparing each of said current average respiration volumes with said reference average respiration volume; and signalling means acuated to indicate the occurrence of apnea whenever a current average respiration volume falls below said reference average respiration volume by a predetermined percentage.

2. Apparatus according to claim 1, further including means for detecting gross body movements of the subject; means for ignoring, from the computations of said reference average respiration volume and said current average respiration volumes, the respiration rate and amplitude of the subject detected when said gross body movements exceed a predetermined magnitude; and means for indicating when said gross body movements are detected.

3. Apparatus according to claim 1, including a manipulatable member for manually presetting said predetermined percentage.

4. Apparatus according to claim 1, further including means for detecting and displaying the heart rate activity of the subject.

5. Apparatus according to claim 1, including a display for displaying the relationship between each of said current average respiration volumes and said reference average respiration volume.

6. Apparatus according to claim 1, further including means for displaying the detected respiration rate.

7. Apparatus according to claim 1, wherein: said electrodes produce an electrical analog signal having a waveform corresponding to the respiration rate and amplitude of the subject; and said computing means comprises a processor for processing said electrical analog signals over the respective time intervals to produce said reference average respiration volume and said current average respiration volumes.

8. Apparatus according to claim 7, further including slope detecting means for detecting the slope of each of said waveforms and for ignoring, from said processor producing said average reference and current respiration volumes, the waveforms wherein said slope detecting means detects slopes exceeding a predetermined magnitude indicating excessive gross body movements.

* * * * *